United States Patent [19]
Kinast

[11] Patent Number: 5,995,858
[45] Date of Patent: Nov. 30, 1999

[54] PULSE OXIMETER

[75] Inventor: Eric Kinast, Westwood, N.J.

[73] Assignee: Datascope Investment Corp., Montvale, N.J.

[21] Appl. No.: 08/969,407

[22] Filed: Nov. 7, 1997

[51] Int. Cl.$^6$ ...................................................... A61B 5/00
[52] U.S. Cl. ............................................................ 600/323
[58] Field of Search ................................. 600/310, 322, 600/323, 330, 473, 476; 356/41, 432, 433; 250/339.12, 341.1

[56] References Cited

U.S. PATENT DOCUMENTS

| | | |
|---|---|---|
| 4,807,630 | 2/1989 | Malinouskas . |
| 4,848,901 | 7/1989 | Hood, Jr. ................................. 356/41 |
| 4,972,331 | 11/1990 | Chance ................................... 600/310 |
| 5,349,952 | 9/1994 | McCarthy et al. ...................... 600/310 |
| 5,368,224 | 11/1994 | Richardson et al. . |
| 5,555,882 | 9/1996 | Richardson et al. . |
| 5,774,213 | 6/1998 | Trebino et al. ........................... 356/41 |
| 5,800,348 | 9/1998 | Kaestle ................................... 600/322 |

Primary Examiner—Eric F. Winakur
Attorney, Agent, or Firm—Abraham P. Ronai

[57] ABSTRACT

An improved pulse oximeter incorporating an innovative method for exposing a patient's extremity to electromagnetic radiation of two wavelengths, e.g., a red wavelength and an IR wavelength, and detecting the absorbance of the extremity at each of the wavelengths, said method comprising the steps of:

(a) generating overlapping first and second pulse trains of electromagnetic radiation having first and second wavelengths and having the same frequency but differing in phase by 90 degrees;

(b) exposing the extremity to the first and second pulses;

(c) producing an electrical signal corresponding to the electromagnetic radiation intensity of both the first and second pulses added together;

(d) amplifying said electrical signal using a tuned amplifier; and (e) demodulating said electrical signal using the first pulse and second pulse, independently, as reference signals. In an alternate embodiment of the invention, improved rejection of noise is provided by using pseudo random sequences for the LED drives and the demodulator reference signals.

6 Claims, 4 Drawing Sheets

PULSE OXIMETER

BACKGROUND OF THE INVENTION

1. Field of the Invention

The invention relates to oximeters which measure levels of blood oxygenation and, in particular, to a plethysmograph system for pulse oximetry having a reduced noise sensitivity.

2. Description of the Prior Art

Oximeters are photoelectric devices which measure the oxygen saturation of blood. Historically, these devices were first used in clinical laboratories on samples of blood taken from patients. In recent years, non-invasive oximeters have been developed and are now widely used in intensive care units to monitor critically ill patients and in operating rooms to monitor patients under anesthesia. Early non-invasive devices relied on dialization of the vascular bed in, for example, the patient's ear lobe to obtain a pool of arterial blood upon which to perform the saturation measurement. More recently, non-invasive devices known as "pulse oximeters" have been developed which rely on the patient's pulse to produce a changing amount of arterial blood in, for example, the patient's finger or other selected extremity. See Yelderman et al., "Evaluation of Pulse Oximetry", *Anesthesiology*, 59:349–353 (1983), and Mackenzie, N., "Comparison of a Pulse Oximeter with an Ear Oximeter and an In-Viv Oximeter", *J. Clin. Monit.*, 1:156–160 (1985).

Pulse oximeters measure oxygen saturation by (1) passing light of two more selected wavelengths, e.g., a "red" wavelength and an "IR" wavelength, through the patient's extremity, (2) detecting the time-varying light intensity transmitted through the extremity for each of the wavelengths, and (3) calculating oxygen saturation values for the patient's blood using the: Lambert-Beers transmittance law and the detected transmitted light intensities at the selected wavelengths.

Prior to the present invention, the patient's extremity has been exposed to the selected wavelengths sequentially, that is, a first light source, such as, a red-emitting LED, has been turned on for a period of time and then turned off, and then a second light source, such as, an IR-emitting LED, has been turned on and then off. See, for example, U.S. Pat. No. 4,167,331 and 4,407,290. Alternatively, it has been proposed to pass broadband light through the extremity and separate the transmitted light into two components using appropriate filters. See U.S. Pat. No. 3,998,550.

Each of these approaches lead to complex and/or expensive devices. For example, filters which are able to adequately separate IR from red light are generally expensive. Also, two light sensors, one for each wavelength, are required for the filter approach. Accordingly, with this approach it is difficult to produce an inexpensive, disposable sensor module, as is required for operating room and other uses.

In the case of the sequential exposure approach, the apparatus must keep track of which light source is active. This involves deploying switches throughout the signal processing portion of the apparatus whose states are changed as the different sources become active. In addition, delay or "dead" times must be incorporated in the system to ensure that the measured transmittance relates to just the source which is currently active and not to a combination of the two sources. Moreover, the sources must be switched rapidly and the delay times must be kept short so that within each on-off/on-off cycle, the amount of blood and other characteristics of the patient's extremity remain essentially constant.

In addition to the foregoing, both approaches suffer from interference problems due to ambient light and signals produced by random electrical and optical energy sources. In particular, changing amounts of ambient red and/or IR radiation can lead to errors in the oxygen saturation measurement. Both of these radiations are normally present in, for example, an operating room as a result of general lighting and the presence of active electrical equipment. Variations in the levels of these radiations at the location of the oximetry sensor can result from such simple activities as movement of personnel or equipment within the operating room. Moreover, even constant amounts of these background radiations pose problems for existing oximeters since they saturate the sensor and/or lead to low signal to noise ratios.

Development of an oximeter with a high signal-to-noise ratio is extremely important. Currently, pulse oximeters are not very useful in the treatment of some of the sickest people. Lowering of the pulse decreases the signal-to-noise ratio, and therefore, negatively affects the oximeter reading. Patients that have cardiac problems or that are very cold have weak pulses. The elderly generally have very weak pulses in the extremities. There has also been great difficulty in using a pulse oximeter to measure the oxygen saturation of a fetus. If a pulse oximeter, less susceptible to noise, could be developed, it would be capable of providing a reading even when a patient has a weak pulse, and would thereby make pulse oximetry available to a larger population of patients.

In an attempt to deal with the ambient radiation problem, existing oximeters have incorporated complicated circuitry to compensate for background radiation and have placed the sensors in hoods or other packages designed to minimize the amount of ambient light which can reach the sensor element.

In addition to the ambient radiation problem, existing oximeters are also highly sensitive to signals created by electrical apparatus. Electrical devices in hospitals, such as electro-surgical instruments, can generate radio frequency signals that a plethysmograph system can pick up. It is desirable then to minimize the sensitivity of the system to interfering signals from sources of this nature.

A known technique for minimizing the interfering signals described above is to alternately drive the light sources by a signal having a frequency which is not present in artificial light or characteristic of other medical instrumentation. While effective for rejecting unwanted signals, the energization of the light sources in alteration by the driving signal mandates that the detector be synchronized with the driving signal for correct demodulation. As the following discussion will show, this arrangement requires undesired widening of the receiver bandwidth resulting in an introduction of noise to the system.

A second known technique for eliminating the interfering signals described above is disclosed in U.S. Pat. No. 5,555,882. This technique involves scanning each demultiplexor frequency to determine which has the lowest associated noise. The noise level, associated with the operating frequency, is used to determine the signal-to-noise ratio of the pulse oximeter signals and thereby qualify certain signals from the pulse oximeter. Those pulses associated with a signal-to-noise ratio below a predetermined threshold are rejected and excluded from use in calculating blood oxygen saturation. This technique reduces noise to a certain extent, however, where several interference sources exist, the selection of the optimal modulation frequency can be extremely difficult.

A third known technique for reducing noise in pulse oximeters is disclosed by U.S. Pat. Nos. 4807630 and 4848901. This technique involves the use of dual drive frequencies for the LEDs. This technique has a number of drawbacks. First, implementation of this technique requires the use of a pair of bandpass filters, thereby increasing the cost of the oximeter. Second, use of this technique requires the introduction of a second modulation frequency, which on its own may make the system more receptive to noise. Third, treating the two modulation frequencies differently (giving them different frequencies) may prevent cancellation of error when the red signal and the IR signal are eventually divided by the microprocessor.

A simpler and more effective solution to the interference/noise problem is to adopt an alternate modulation scheme which allows the use of a narrow-band photodetector amplifier. Use of such an amplifier completely avoids the generation of spurious response lobes, as will be discussed in further detail below. Since sensitivity is restricted to a narrow band of frequencies, there is much less opportunity for noise to enter the system. Further, the analysis of harmonics and selection of the optimal modulation frequency is much simplified.

The above mentioned solution may also be useful in improving the design of oximeters incorporating a reflectance sensor which uses back scattered rather than transmitted light. A pulse oximeter incorporating a reflectance sensor has a much smaller amplitude signal to work with. Consequently, a reduction in noise would be extremely useful for such an oximeter.

SUMMARY OF THE INVENTION

It is an object of the invention to produce a pulse oximeter that displays an improved rejection of noise from electromagnetic interference and ambient light.

It is another object of the invention to produce a pulse oximeter in which phase, rather than frequency, is used to distinguish the red and infra-red modulation.

It is a further object of the invention to produce a pulse oximeter incorporating a photodetector amplifier having a narrower bandwidth than the prior art and, thus, providing improved rejection of noise.

It is yet a further object of the invention to produce a pulse oximeter providing improved rejection of noise by using pseudo random sequences for its LED drive and demodulator reference signals.

It is still yet a further object of the invention to produce a pulse oximeter capable of providing an accurate oxygen saturation reading even when a patient has a weak pulse.

To achieve the foregoing and other objects, the invention, in accordance with certain of its aspects, provides an improved method for exposing a patient's extremity to electromagnetic radiation of two wavelengths, e.g., a red wavelength and an IR wavelength, and detecting the absorbance of the extremity at each of the wavelengths, said method comprising the steps of:

(a) simultaneously generating first and second pulse trains of electromagnetic radiation having first and second wavelengths and having the same frequency but differing in phase by 90 degrees;

(b) exposing the extremity to the first and second pulses;

(c) producing an electrical signal corresponding to the electromagnetic radiation intensity of both the first and second pulse trains added together;

(d) amplifying said electrical signal using a tuned amplifier; and (e) demodulating said electrical signal using the first pulse train and second pulse train, independently, as reference signals.

In accordance with other of its aspects, the invention provides apparatus for practicing the foregoing method which comprises:

(a) a first light pulse generator, modulated by a first pulse signal, for generating pulses of light;

(b) a second light pulse generator, modulated by a second pulse signal, which is 90 degrees out of phase with the first pulse signal, for generating pulses of light;

(c) means for exposing the patient's extremity to the first and second pulses of light, e.g., means for attaching a red and an IR LED to the patient's finger;

(d) a photodetector, responsive to electromagnetic radiation produced by the first and second light pulse generators, for producing an electrical signal which is representative of the electromagnetic radiation intensity at a recording location near the patient's extremity;

(e) a tuned amplifier for amplifying said electrical signal;

(f) a first demodulator for extracting the first pulse signal from the amplified electrical signal;

(g) a second demodulator for extracting the second pulse signal from the amplified electrical signal; and (h) a pair of lowpass filters to restrict the response of the demodulator to the physiological bandwidth.

In an alternate embodiment of the invention, improved rejection of noise is provided by using pseudo random sequences for the LED drives and the demodulator reference signals.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

A pulse oximeter sensor (probe) commonly consists of two LEDs of different wavelengths, one each in the red and infrared (IR) bands, and a photodetector. When the sensor is applied to the patient, the radiation from the LEDs passes through, or is scattered back from, the patient's tissue, and then impinges on the photodetector. During interaction with the tissue, the radiation is attenuated. The degree of attenuation is modulated by the patient's pulsatile blood flow, and is also influenced by the blood's oxygen saturation. The pulse oximeter instrument is able to compute the oxygen saturation from an analysis of this pulsatile modulation, measured independently at each wavelength.

Since both wavelengths share a single photodetector, it is necessary to provide means for uniquely identifying and separating the photodetector signal components attributable to each LED. In conventional oximeters, this means takes the form of a time domain multiplexing scheme, implemented by pulsing each LED during specific time windows. Each LED is sequentially energized for brief non-overlapping intervals as part of a repetitive cycle. Periods where neither LED is energized are provided at least once per cycle, providing means for the rejection of ambient light. Rejection of ambient light involves measuring the intensity of the ambient light and then subtracting this value from the measured intensities of the red and IR light.

Figure 1:
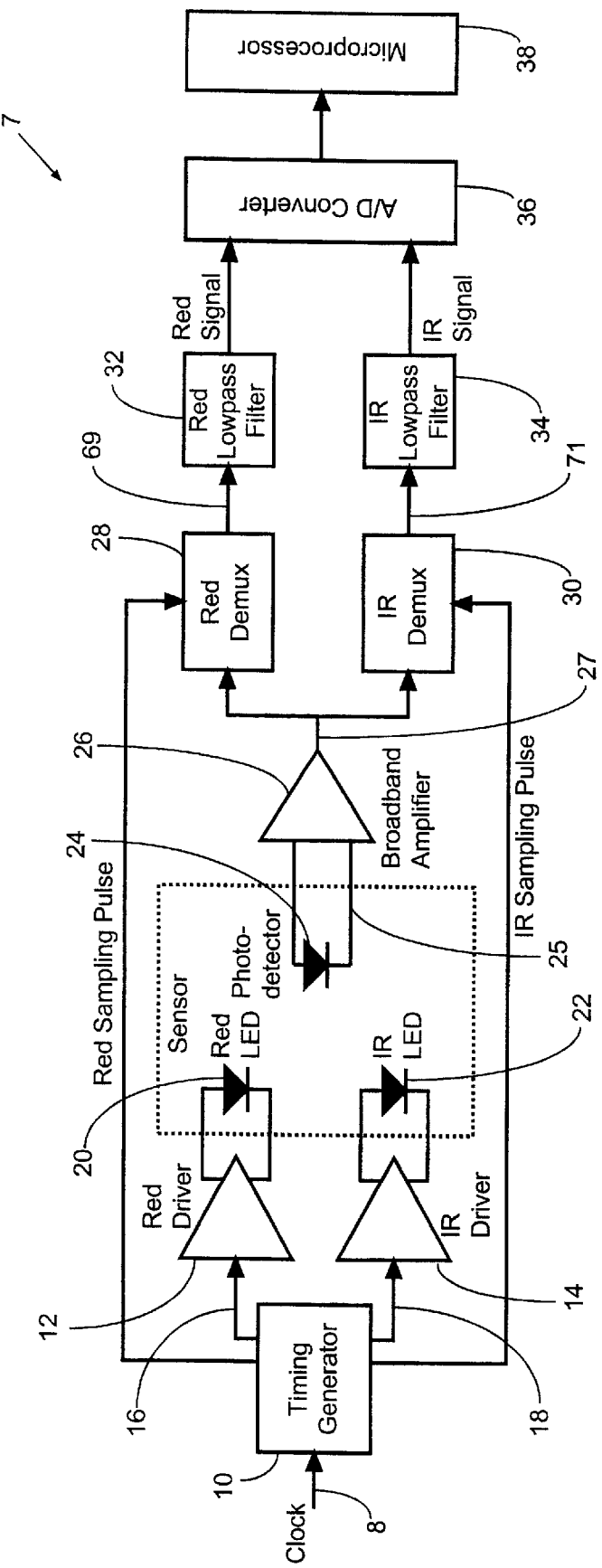
FIG. 1 is a block diagram of a prior art oximeter employing a sequential exposure approach.

FIG. 1 illustrates a prior art pulse oximeter 7 employing a sequential exposure approach. A timing generator 10 has a clock input signal 8 and outputs a first signal 16 to a red driver 12, a second signal 18 to an IR driver 14, a third signal, labeled red sampling pulse, to a red demodulator 28, and a fourth signal, labeled IR sampling pulse, to an IR demodulator 30. The red driver 12 excites a red LED 20, which creates a red light, at an amplitude and frequency dictated by the first signal 16. The IR driver 14 excites an IR LED 22, which creates IR light, at an amplitude and frequency dictated by the second signal 18. The red and IR light are never active at the same time. A photodetector 24 receives both the red and the IR light and generates a photodetector signal 25. Said photodetector signal 25 is amplified by a broadband amplifier 26 which communicates an amplified photodetector signal 27 to the red demodulator 28 and the IR demodulator 30. The amplified photodetector signal 27 is allowed to pass through each of the demodulators at specific times determined by the timing generator 10. During the period of time dedicated towards measurement of the red light, the timing generator 10 sets the value of the red sampling pulse signal such that the amplified photodetector signal 27 is allowed to pass through the red demodulator 28. The red demodulator 28 then communicates a demodulated and amplified photodetector red prefilter signal 69, containing information regarding the red light emitted by the red LED 20, to a red lowpass filter 32, which in turn generates a signal, labeled Red Signal. During the period of time dedicated towards measurement of the IR light, the timing generator 10 sets the value of the IR sampling pulse signal such that the amplified photodetector signal 27 is allowed to pass through the IR demodulator 30. The IR demodulator 30 then communicates a demodulated and amplified photodetector IR prefilter signal 71, containing information regarding the IR light emitted by the IR LED 22, to an IR lowpass filter 34, which in turn generates a signal, labeled IR signal. An analog-to-digital converter 36 receives the Red Signal and the IR Signal and communicates the digital version of these signals to a microprocessor 38 which calculates the blood oxygen saturation of the patient.

Figure 2:
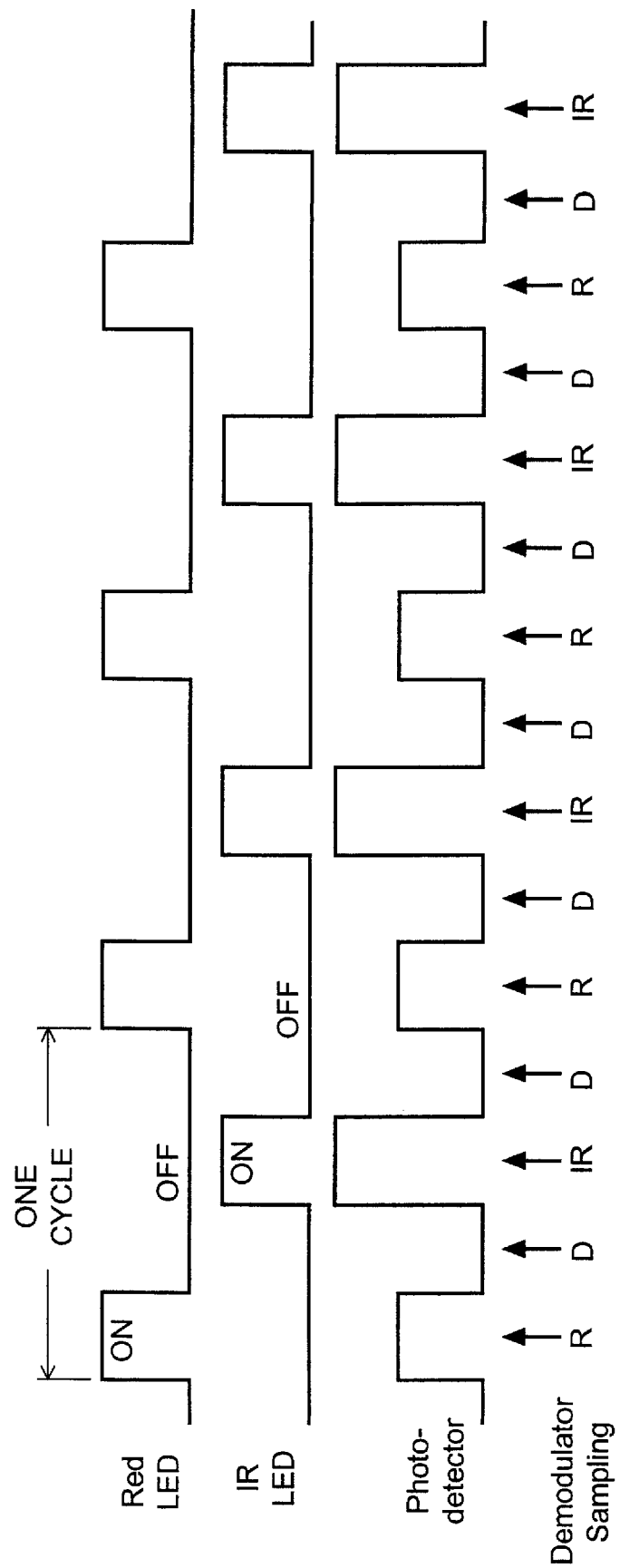
FIG. 2 is a timing diagram illustrating the prior art method of driving the red and IR LEDs.

The prior art method of driving the red and IR LEDs is illustrated in FIG. 2. The top trace, labeled Red LED, represents the periods during which the red LED is energized. The middle trace, labeled IR LED, shows the periods during which the IR LED is energized. The bottom trace shows the photodetector signal. In this example, the IR LED is shown causing a somewhat larger photodetector signal than the red LED, indicating that more IR light passed through the patient's tissue than red light. Dark periods, during which neither LED is energized, are interspersed between the red and IR periods to permit compensation for ambient light. Some commercial implementations utilize two dark periods per cycle, as shown in FIG. 2, while others omit one of the two dark periods. If ambient light were to impinge upon the photodetector, the ambient light signal would be added during all periods. Therefore, the true intensity of red or IR light emitted by the LEDs and passed through the patient's tissue can be obtained by subtracting the signal observed during the dark periods.

The portions of the photodetector signal 25, as shown in FIG. 1, due to the red and IR light are recovered by means of the red demodulator 28 and the IR demodulator 30, respectively. The red demodulator 28 samples the photodetector signal 25 at approximately the times indicated by the vertical arrows designated "R." The IR demodulator 30 samples the photodetector signal 25 at approximately the times indicated by the vertical arrows designated "IR." To provide rejection of ambient light, the demodulators further sample the photodetector signal 25 at approximately the times indicated by the vertical arrows marked "D", the demodulators being arranged so as to subtract these samples from the adjacent red and IR samples. In the case where the ambient light is essentially constant, and changes only negligibly between samples, this technique ideally provides complete cancellation of the ambient light signal. However, if the intensity of the ambient light were to change significantly between samples, only a partial rejection of the ambient light occurs. As most artificial light sources are operated from the alternating current mains, their optical output generally contains fluctuations at frequencies which are harmonics of the mains frequency. For some common types of lamps these fluctuations can be quite strong; for example, ordinary fluorescent lamps operated in areas with a 60 Hz power supply have a pronounced flicker at 120 Hz. To provide effective rejection of flickering ambient light, a modulation frequency much greater than the effective frequency must be used. Drive frequencies on the order of a few kHz are therefore generally employed.

The red and IR LEDs are conventionally driven by square waves which cyclically turn the red and IR LEDs on and off. The red driver and the IR driver are not on at the same time. In fact, there is generally a "dead" period, during which neither the red or the IR LEDs are on, to ensure no cross talk between the red and IR photodetector signals. The broad band amplifier 26, as shown in FIG. 1, used to amplify both the red and IR light needs to have a broad bandwidth in order to accurately amplify a square wave. This is easily understood if one pictures the square wave as the superpositioning of many sinusoidal waves. In order for the amplifier to accurately amplify the square wave it must have a bandwidth wide enough to encompass a large number of the Fourier expansion terms of the square wave. If the amplifier bandwidth is too small then the only the terms of the Fourier expansion within the bandwidth will be amplified, distorting the waveshape, causing an error in the light intensity measurement. However, if a large amplifier bandwidth is used, to ensure the accuracy of the waveshape, the oximeter becomes more noise vulnerable because many different external signals, having frequencies within the bandwidth of the amplifier, may enter the system. In order to pass pulses generated by a modulation frequency of a few kHz, as was determined earlier to be commonly used to avoid flickering light problems, the amplifier may require a bandwidth as great as 10 kHz or more. The improved pulse oximeter herein disclosed is less noise prone because it is capable of using an amplifier having a much narrower bandwidth.

Figure 3:
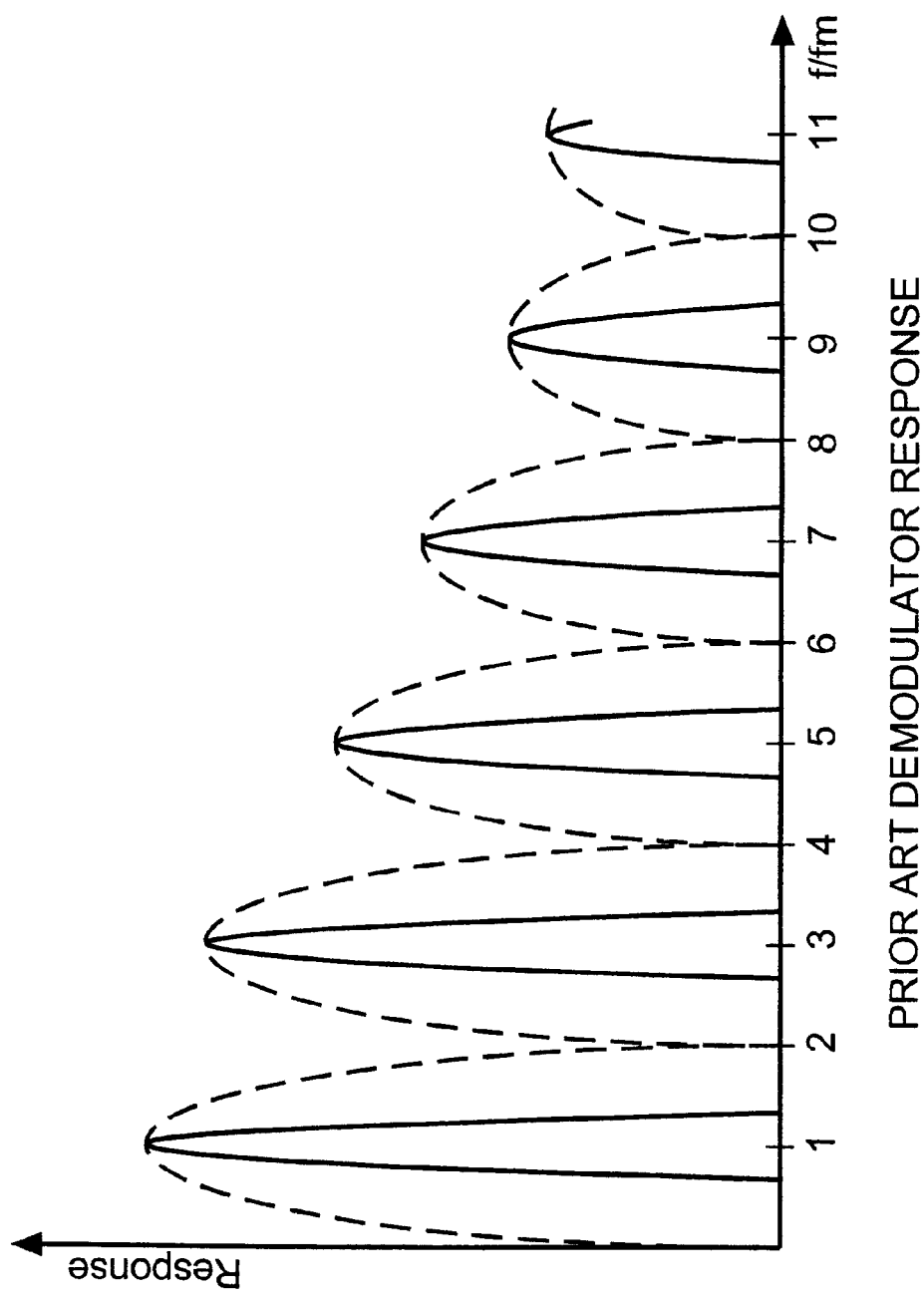
FIG. 3 illustrates a plot of a prior art demodulator response, labeled Response, and the frequency of the amplifier output signal divided by the modulation frequency, labeled f/fm.

FIG. 3 illustrates a plot of a prior art demodulator response, labeled Response, versus the frequency of the amplifier output signal divided by the modulation frequency, labeled f/fm. The dotted line represents the output of the demodulator (the demultiplexing means), which exhibits a series of response lobes centered about odd harmonics of the modulation frequency. The solid line represents the overall response of a prior art demodulator when a low pass filter is also considered. The filter has the effect of narrowing the lobes, the width being determined by the low pass filter's bandwidth. If the width of the amplifier bandwidth was increased then more spurious lobes would appear on the plot. Each of these lobes represents a region of noise sensitivity.

Figure 4:
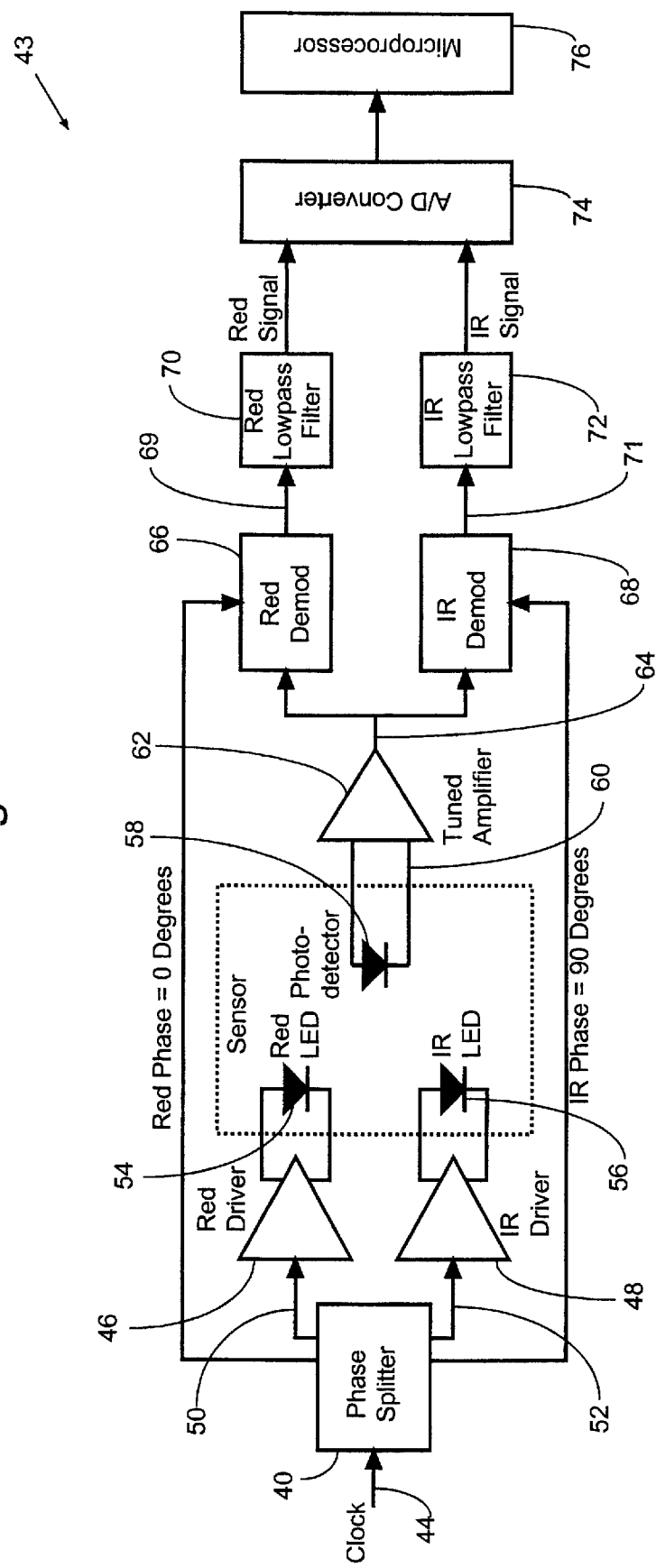
FIG. 4 is a block diagram of the preferred embodiment of the current invention.

FIG. 4 illustrates a block diagram of an improved pulse oximeter 43. A phase splitter 42 has a clock input signal 44 and outputs a first signal 50 to a red driver 46, a second signal 52 to an IR driver 48, a third signal, labeled Red Phase=0 Degrees, to a red demodulator 66, and a fourth signal, labeled IR Phase=90 Degrees, to a IR demodulator 68. The third and fourth signals are identical except that the fourth signal has a phase shift of 90 degrees. Similarly, the first and second signals are identical except that the second signal has a phase shift of 90 degrees. A preferred drive waveform for the red driver 46 and the IR driver 48 is a 50% duty cycle square wave, on account of the ease of generation. By well known techniques, the drive waveform for the red driver 46 and the IR driver 48 can be readily generated from a clock of twice the drive frequency. However, other wave shapes may be employed by the use of suitable generation and phase splitting circuits. The red signals (signal one and three) are arbitrarily assigned a 0 degrees phase and the IR signals (signals two and four) a 90 degrees phase. The red driver 46 delivers a well controlled current, modulated by the first signal (the red drive waveform), to a red LED 54, which creates a red light. The red driver 46 is still delivering current, the IR driver 48 delivers a well controlled current, modulated by the second signal (the IR drive waveform), to an IR LED 56, which creates an IR light. Since the red driver 46 and the IR driver 48 differ in phase by 90 degrees, the periods of illumination of the red LED 54 and the IR LED 56 partially overlap in time. The LED currents may be of fixed amplitude, or may be made variable, as a means of extending the dynamic range of the system. The red and IR light combine in the tissue of a patient (in the illustrated dotted box area). A photodetector 58 receives the combined red and IR light and generates a photodetector signal 60. The photodetector signal 60 is amplified by a tuned amplifier 62. Said tuned amplifier 62 generates an amplified photodetector signal 64 and communicates said signal to a red demodulator 66 and an IR demodulator 68. The red demodulator 66 communicates a demodulated and amplified photodetector red prefilter signal 69 containing information regarding the intensity of the red light emitted by the red LED 54, to a red lowpass filter 70. The third signal, labeled Red Phase=0 Degrees, is used by the red demodulator 66 as a reference signal to generate the red prefilter signal 69. The red lowpass filter 70 generates a signal, labeled Red Signal. The IR demodulator 68 communicates a demodulated and amplified photodetector IR prefilter signal 71, containing information regarding the intensity of the IR light emitted by the IR LED 56, to an IR lowpass filter 72. The fourth signal, labeled IR Phase=90 Degrees, is used by the IR demodulator 68 as a reference signal to generate the IR prefilter signal 71. The IR lowpass filter 72 generates a signal labeled IR Signal. An analog-to-digital converter 74 receives the Red Signal and the IR Signal and communicates the digital version of these signals to a microprocessor 76 which calculates the blood oxygen saturation of the patient.

In various other implementations, the lowpass filters may constitute part of the analog-to-digital converter 36, such as the decimation filters of delta-sigma converters. Alternatively, the filtering may be performed by software or other digital means, following the analog-to-digital conversion. As accurate matching of the red and IR lowpass filter responses is required for good overall accuracy of the oximeter, such digital filtering means may prove advantageous, as digital filters inherently provide exact matching. Further, in some implementations, the demodulation function may be integrated into the analog-to-digital converter 36, as by synchronizing the acquisition of samples with the demodulation reference phase. Furthermore, assuming the existence of a sufficiently fast analog-to-digital converter and the availability of sufficient computing power in a microprocessor or an equivalent, it is possible to directly digitize the amplifier output and to perform the operations of demodulation and filtering by purely digital means.

The improved pulse oximeter takes advantage of orthogonal waves differing in phase by 90 degrees. The red driver 46 and the IR driver 48, of the improved pulse oximeter 43, are driven with waveforms of identical wave shape, but which are in quadrature i.e. differ in phase by 90 degrees. The photodetector signal 60 is acquired by the tuned amplifier 62 having a filter with a relatively narrow bandpass centered about the red driver 46 and the IR driver waveform's fundamental frequency. The output of this tuned amplifier 62 is a sinusoid, the amplitude and phase of which depend on the intensities of the red and IR optical signals reaching the photodetector 58. The portions of the photodetector signal 60 representing the red and IR light intensities are recovered from the amplified photodetector signal 64 by means of two synchronous demodulators (the red demodulator 66 and the IR demodulator 68), which are responsive to signals of a certain phase, and reject signals in quadrature. Thus, the red demodulator 66 responds only to the red signal components, but rejects the IR signal components, as these are in quadrature to the demodulation phase. Similarly, the IR demodulator 68 responds only to the IR signal components, and rejects the red signal components.

To illustrate this principle, consider that the red driver 46 and the IR driver 48 produce waveforms identical in form, but shifted in phase by 90 degrees, and that these waveforms exhibit the property of orthogonality. The simplest such waveforms, used in the preferred embodiment, are unipolar square waves of 50% duty cycle. Assume that the red driver is considered to have a phase angle of zero, with the IR driver then having a phase of 90 degrees, with the frequency of the waveform being ω radians per second. Assume that the amplitude of the red waveform, upon being received by photodetector 58 and reaching amplifier 62 is A and that the amplitude of the IR waveform at this same location is B. By means of Fourier expansion, these red and IR waveforms can be expressed as:

$$red = A\left[0.5 + \frac{2}{\pi}\sin(\omega t) + \frac{2}{3\pi}\sin(3\omega t) + \frac{2}{5\pi}\sin(5\omega t) + ...\right] \quad (1)$$

$$IR = B\left[0.5 + \frac{2}{\pi}\cos(\omega t) - \frac{2}{3\pi}\cos(3\omega t) + \frac{2}{5\pi}\cos(5\omega t) + ...\right] \quad (2)$$

where t is the time in seconds, and the term 0.5 results from the fact that the waveforms are unipolar, that is, it reflects the DC component of the waveform. However, the tuned amplifier 62, by virtue of its narrow bandpass centered about the frequency ω, will reject all terms except for those containing sin(ωt) or cos(ωt). Since the two expressions above are superimposed at the input to the tuned amplifier, the amplifier's output 64 can therefore be expressed as:

$$G\frac{2}{\pi}[A\sin(\omega t) + B\cos(\omega t)] \quad (3)$$

where G is the midband gain of amplifier 62. Note that although the original drive signals were square waves, the effect of the tuned amplifier has been to preserve only two simple sinusoidal waveform components.

We may now consider the demodulation of this signal by means of multiplication by a reference waveform. Assume the red reference signal to be of the form sin(ωt). The red demodulator 66 would then multiply the above expression by sin(ωt), yielding a red prefilter signal 69 which may be expressed as:

$$G\frac{2}{\pi}[A\sin^2(\omega t) + B\cos(\omega t)\sin(\omega t)] \quad (4)$$

The red lowpass filter 70 has the effect of averaging the red prefilter signal 69 over many cycles of the frequency ω. By inspection, sin²(ωt) has a value of 0.5 when averaged over many cycles, while sin(ωt)cos(ωt) has a value of zero when so averaged. Therefore, the red signal subsequent to the red lowpass filter 70 is G/π times A, and does not contain B. The factor of 1/π is of no consequence, as it can be eliminated by adjustment of the value of G. Therefore, demodulation by multiplication by a reference signal of the form sin(ωt) has recovered the red signal intensity A from the mixed signal presented to the amplifier.

If the amplifier output 64 is similarly multiplied by a reference signal of the form cos(ωt) in IR demodulator 68, an IR prefilter signal 71 results, which may be expressed:

$$G\frac{2}{\pi}[A\sin(\omega t)\cos(\omega t) + B\cos^2(\omega t)] \quad (5)$$

Similarly, by inspection, cos²(ωt) has a value of 0.5 when averaged over many cycles, and sin(ωt)cos(ωt) remains zero when so averaged. Therefore, the IR signal subsequent to the IR lowpass filter 72 is G/π times B, and does not contain A. Therefore, red and IR intensities A and B can be recovered from the mixed signal 60 by demodulation using reference signals of sin(ωt) and cos(ωt), respectively.

The practical construction of the demodulators 66 and 68 can be simplified if square waves, rather than sinusoids, are used for the reference signals. Such a demodulator can use simple switching elements, rather than linear multiplying elements, in its construction, with an attendant simplification of design. In this case, the reference signals take the forms of 50% duty cycle bipolar square waves, with the demodulation process being equivalent to multiplication by +1 or −1, according to the state of the square waves. The reference signal for red demodulator 66 ideally has identical phase to that of red driver signal 50, while the reference for the IR demodulator 68 ideally has identical phase to that of IR driver signal 52.

The use of square waves for the demodulator reference does introduce an adverse effect, in that the demodulator will show sensitivity to inputs at frequencies other than ω. In fact, the demodulator will present a response lobe, known as a spurious lobe, at all frequencies where the Fourier expansion of the reference waveform has non-zero terms. However, the waveshapes of the reference signals are identical to those of the drive signals, and therefore have the same terms in their Fourier expansions. It has already been noted that the tuned amplifier 62 passes only the fundamental frequency ω of these drive signals, and rejects all other Fourier expansion terms. Therefore, no signals corresponding to the spurious response lobes will be delivered to the demodulators. Therefore, the composite of tuned amplifier 62 and demodulators 66 and 68 exhibits only a single response lobe centered about fundamental frequency ω. This is in contrast to the prior art, in which demodulators, also exhibiting spurious responses, were preceded by a wideband amplifier, which did not eliminate many of these undesirable response lobes. The single, narrow, response lobe of the improved art reduces the susceptibility of the system to noise.

When the pulsatile blood flow modulates the amplitudes A and B, modulation sidebands are produced, as in any amplitude modulation process. Therefore, the bandwidth of the tuned amplifier 62, as shown in FIG. 4, must be wide enough to at least pass these sidebands. In typical pulse oximeters, the useful frequency components of the physiological signal are considered to occupy a bandwidth of roughly 20 Hz. Therefore, the bandpass of the amplifier must extend at least on the order of ±20 Hz around the LED drive frequency. However, the amplifier must pass the signals without significant phase shift, lest inaccurate demodulation and crosstalk between the red and IR channels result. With practical filters, this is achieved only when the amplifier response is symmetrical and accurately centered on the LED drive frequency. The accuracy to which the amplifier must be tuned is a function of its bandwidth, such that a broader bandwidth requires less critical tuning. Therefore, practical considerations suggest that the amplifier bandpass be made somewhat larger than the minimum imposed by the sideband considerations. However, the bandpass would still be much less than is required by conventional time division multiplex systems. For example, a bandwidth on the order of 100 Hz might be used for a practical tuned amplifier, which is much less than the several kHz required in conventional systems.

However, the tuned amplifier 62 does not act alone in determining the system bandpass. The bandpass is further refined by low pass filters 70 and 72. These filters are generally made just wide enough in bandwidth to pass the range of physiological frequencies of interest. Although the demodulators 66 and 68, when considered alone, exhibit broad response lobes, the combination of a demodulator and its associated low pass filter exhibits a narrower response, the half-width being determined by the cutoff frequency of the low pass filter. To achieve the noise reduction advantages of the new art, the signal chain consisting of tuned amplifier 62, demodulators 66 and 68, and low pass filters 70 and 72 must collectively produce only a single response lobe centered about the fundamental frequency. This can be seen to be the case so long as the response of tuned amplifier 62 is sufficiently narrow to exclude frequencies corresponding to the narrow spurious response lobes of the demodulator/filter combination. The system will then exhibit a single response lobe just wide enough to pass the physiological signals, producing maximum exclusion of noise.

Despite due care in the design and implementation of the tuned photodetector amplifier 60, as shown in FIG. 4, some residual phase error is inevitable in practice. This is due to the unavoidable propagation delays which occur in all electronic circuits, as well as the difficulty in precisely tuning the amplifier. Small residual phase errors will cause crosstalk between the red and IR channels. That is, if the phase of the amplified photodetector signal 64, as shown in FIG. 4, were to be displaced by a small angle δ from its demodulation axis, the response in its associated demodulator would be reduced by a factor of cos δ, while a spurious response with relative amplitude sin δ would appear in the other demodulator. This may be illustrated by again considering the case of multiplication by reference signals of the form sin(ωt) and cos(ωt). Consider that a constant phase error δ is added to both reference signals, so that they become sin(ωt+δ) and cos(ωt+δ). By the use of the trigonometric formulae for the sum of angles, these may be expanded to the following expressions:

$$\sin(\omega t+\delta)=\sin(\omega t)\cos(\delta)+\cos(\omega t)\sin(\delta) \qquad (6)$$

$$\sin(\omega t+\delta)=\cos(\omega t)\cos(\delta)-\sin(\omega t)\sin(\delta) \qquad (7)$$

The prefilter signal 69 produced by red demodulator 66 may be obtained by multiplication of the amplifier output signal 64 by the reference signal including phase error δ, which is computed by multiplying equation (3) by the expansion of equation (6), with the following result:

$$G\frac{2}{\pi}[A\sin^2(\omega t)\cos(\delta) + A\sin(\omega t)\cos(\omega t)\sin(\delta) + B\cos(\omega t)\sin(\omega t)\cos(\delta) + B\cos^2(\omega t)\sin(\delta)] \qquad (8)$$

Once again, the low pass filter 70 has the effect of averaging over many cycles of ω. As was noted before, $\sin^2(\omega t)$ and $\cos^2(\omega t)$ have a value of 0.5 when averaged over many cycles, while $\sin(\omega t)\cos(\omega t)$ has an average value of zero. Therefore, the filtered red signal may be written:

$$\frac{G}{\pi}[A\cos(\delta) + B\sin(\delta)] \qquad (9)$$

Note that in the limiting case of no phase error, where δ is zero, equation (9) becomes simply G/π times A, as was derived in the preceding ideal analysis. Similarly, for the IR demodulator 68 we multiply equation (3) by the expansion of equation (7), and similarly account for the action of low pass filter 72, with the result that the IR filtered signal may be expressed:

$$\frac{G}{\pi}[B\cos(\delta) - A\sin(\delta)] \qquad (10)$$

The expression (9) for the red filtered signal ideally contains only the red signal A, and not the IR signal B. Therefore, the term Bsin(δ) represents the crosstalk error of the IR signal into the red signal. Note that this error is proportional to the sine of the phase error angle. Similarly, the expression (10) for the filtered IR signal ideally contains only the IR signal B, the term Asin(δ) being the crosstalk error of the red signal into the IR signal. In this case, it has been assumed that the phase error is identical in both the red and IR channels. However, in practice this may not be the case, in which event δ will assume different values in equations (9) and (10).

Consider the case of the red channel when a phase error of 5 degrees is introduced. The amplitude of the signal recovered by the red demodulator would fall to approximately 99.6% and a spurious signal (caused by the term that does not drop out), having an amplitude of approximately 8.7% of the red amplitude would be introduced into the IR demodulator. This spurious signal would constitute a crosstalk of about 8.7% of the red signal into the IR channel.

In the case of this example, the slight reduction in the demodulated red signal amplitude is of no consequence, as the pulse oximeter computation algorithm generally includes normalization of the signal amplitudes. However, the crosstalk into the IR channel is highly objectional, as this will impact the accuracy of the saturation computed by the oximeter. Therefore, some means of compensation, preferably automatic, is required.

One possible means of compensation is to provide adjustment of the tuning of the amplifier 60, in which the center frequency is adjusted to bring the phase error to zero. A second possible means is to permit adjustment of the phase references used by the demodulators (the red demodulator 66 and the IR demodulator 68) with respect to the LED drive signals (the first signal 50 and the second signal 52). A third possible means is to leave the filter tuning and demodulator phase fixed, and to compensate for any errors after demodulation. This can be achieved by signal subtraction. In the above mentioned case involving a phase error of five degrees, the crosstalk into the IR channel could be compensated by subtraction of 8.7% of the red signal from the IR signal. The red and IR demodulated signals, including crosstalk errors, may be expressed:

$$I_D = I + c_2 R \qquad (11)$$

$$R_D = R + c_1 I \qquad (12)$$

where $R_D$ and $I_D$ are the red and IR demodulated and filtered signals, respectively, including crosstalk, R and I are the ideal red and IR signals, respectively, in the absence of crosstalk, $c_1$ represents the fractional crosstalk of the IR signal into the red signal, and $c_2$ represents the fractional crosstalk of the red signal into the IR signal.

With knowledge of $c_1$ and $c_2$ it would be possible to determine the ideal signals R and I from the available signals $R_D$ and $I_D$. Therefore, a calibration procedure is required by which these constants can be determined. This procedure consists of briefly operating the oximeter with only a single LED active. If only the red LED is active, while the IR LED is inhibited, the ideal IR signal I must be zero, so that $R_D=R$ and $I_D=c_2 R$. Therefore, under these conditions, $c_2$ may be obtained by measuring $R_D$ and $I_D$ and computing the ratio $C_2=I_D/R_D$. Next, the oximeter may be operated with only the IR led active, and the red LED inhibited, forcing the ideal red signal to be zero, so that $R_D=c_1 I$ and $I_D=I$. Under these operating conditions, $c_1$ is obtained by measuring $R_D$ and $I_D$ and computing the ratio $c_1=R_D/I_D$.

Following the determination of $c_1$ and $c_2$, the oximeter may be returned to normal operation, where these constants are used to correct the crosstalk errors. Solving equations (11) and (12) simultaneously for R, we find:

$$R = \frac{R_D - c_1 I_D}{(1 - c_1 c_2)} \qquad (13)$$

Similarly, solving equations (11) and (12) simultaneously for I yields:

$$I = \frac{I_D - c_2 R_D}{(1 - c_1 c_2)} \qquad (14)$$

Therefore, it is possible to recover the ideal signals R and I from the crosstalk-corrupted signals $R_D$ and $I_D$ once the values of $c_1$ and $c_2$ have been determined. In a well-designed system, crosstalk would be minimized, so that $c_1$ and $c_2$ would be expected to have small values. Therefore, the product $c_1 c_2$ would be very small, and the factor $(1-c_1 c_2)$ would be very close to unity, and may therefore be neglected. Although neglecting this factor causes a small error in the amplitude of signals R and I, this is of no consequence, as the known process of calculating the oxygen saturation from these signals effectively normalizes the signal amplitudes.

The above described improved pulse oximeter takes advantage of the basic principle that mixed waveforms can be separated individually by a demodulation process if they are orthogonal functions. The invention employs waveforms that are orthogonal when shifted 90 degrees in phase. The sequential exposure waveforms of the prior art also exhibits orthogonality. One should note, however, that not all waveforms given such a phase shift exhibits orthogonality. The particular waveforms selected in this invention have the additional property that they can be passed through a narrow bandwidth amplifier with no loss in the ability to accurately perform the demodulation, a consideration not shared by the prior art. The narrow bandwidth is the basis of the improved noise rejection of the invention. However, there are other ways of achieving noise immunity besides bandwidth reduction.

The prior art exhibits poor immunity to noise because the reference signals applied to its demodulators (samplers) are pulses, which have a rich frequency spectrum when subject to Fourier analysis. As a result, there are many possible input noise frequencies which may correlate with frequency components of the reference signal, thereby producing an unwanted signal at the output of the demodulator. The invention suffers from the same defect when square waves are used as references, however, the invention allows for the use of a narrow bandwidth amplifier which prevents these troublesome noise frequencies from ever reaching the demodulator.

Accordingly, another method for reducing the systems susceptibility to noise is to choose a reference waveform, such as a sinusoid, which has a poor correlation with the noise. Such a method would work even if the amplifier bandwidth remains very wide. However, effective use of a sinusoid requires the employment of a demodulator which performs true multiplication, rather than the much simpler switching circuits which can be employed when the reference signal takes the form of a train of rectangular pulses. The basic requirements for this reference waveform are:

1) It must correlate with the LED drive signal in its own channel, i.e. the red demodulator must correlate 100% with the red LED.
2) It must have zero correlation with the LED drive signal from the other channel, i.e. the red demodulator must correlate 0% with the IR LED.
3) It must have minimal correlation with noise, but should be a simple train of rectangular pulses, to facilitate demodulator design.

Requirement one can be met by using the same signal for the LED drive and the reference signal. Requirement two simply means that the signals used for the two channels must be orthogonal. For some waveshapes, this may mean a 90 degrees phase shift. Requirement three can be met by using a class of signals, known as pseudo random sequences, for the reference signal. These signals look like noise but are cyclical. The have the property of correlating with themselves but poorly correlating with other signals, such as noise or an interference frequency. It is possible to make orthogonal sets of these waveforms. Pseudo random signals are used in fields such as spread-spectrum and communications and satellite navigation systems like global positioning satellite (GPS).

Referring to FIG. 1, implementation of pseudo random sequences involves programing the timing generator 10 such that the red driver 12 and the IR driver 14 are driven by pseudo random signals. A first pseudo random signal (replacing the third signal 12) is used to drive the red LED 20 and is used in demodulation as the reference signal for the red demodulator 28. A second pseudo random signal is used to drive the red LED 20 (replacing the fourth signal 18) and is used in demodulation as the reference signal for the red demodulator 28. The broadband amplifier 26 must have a bandwidth wide enough to pass the pseudo random signals. Despite the wide bandwidth, however, the system remains low in noise because the demodulation process is now less susceptible to noise.

What is claimed is:

1. Apparatus for use in a pulse oximeter for generating and detecting two wavelengths of electromagnetic radiation comprising:

(a) means for generating pulses of electromagnetic radiation having a first wavelength and for generating pulses of electromagnetic radiation of a second wavelength that have the same frequency as the pulses having the first wavelength and are in quadrature with the pulses having the first wavelength;

(b) means for simultaneously exposing a selected portion of a human being or animal to the first and second pulses;

(c) detector means for producing an electrical signal which is representative of the electromagnetic radiation intensity at a selected location in the vicinity of the selected portion of the human being or animal, said detector means being responsive to electromagnetic radiation including the first and second wavelengths;

(d) amplifying means for amplifying the electrical signal;

(e) demodulating means for extracting the portion of the electrical signal created by electromagnetic radiation having the first wavelength and for extracting the portion of the electrical signal created by electromagnetic radiation having the second wavelength;

(f) filtering means for filtering the portion of the electrical signal created by electromagnetic radiation having the first wavelength and the portion of the electrical signal created by electromagnetic radiation having the second wavelength, said filtering means generates a first signal which indicates the unadjusted amplitude measurement of the electromagnetic radiation having the first wavelength and a second signal which indicates the unadjusted amplitude measurement of the electromagnetic radiation having the second wavelength; and (g) error compensation means which corrects residual phase errors by:
1) briefly operating the oximeter allowing only those pulses of light corresponding to the first wavelength to be emitted;
2) during this time measuring the amplitudes of the first and second unadjusted amplitudes, and computing the fractional crosstalk of the first amplitude into the second;
3) briefly operating the oximeter allowing only those pulses of light corresponding to the second wavelength to be emitted;
4) during this time measuring the amplitudes of the first and second unadjusted amplitudes, and computing the fractional crosstalk of the second amplitude into the first;
5) during normal operation, producing a first corrected signal by subtracting from the first unadjusted amplitude a quantity equal to the second amplitude times the fractional crosstalk of the second amplitude into the first;

6) during normal operation, producing a second corrected signal by subtracting from the second unadjusted amplitude a quantity equal to the first amplitude times the fractional crosstalk of the first amplitude into the second.

2. A pulse oximeter comprising:
a) a waveform generator producing a first drive waveform, a first reference waveform having the same phase and frequency as the first drive waveform, a second drive waveform, and a second reference waveform having the same phase and frequency as the second drive waveform, the second waveforms being identical in frequency and waveshape to the first waveforms but differing in phase by 90 degrees;
b) first and second electro-optical emitters respectively energized by the first and second drive waveforms, said first and second electro-optical emitters producing electromagnetic radiation having first and second wavelengths, respectively;
c) a photodetector responsive to radiation of said first and second wavelengths and arranged to receive radiation from said first and second emitters after said radiation has interacted with body tissue;
d) an amplifier for receiving a signal generated by said photodetector and for producing an amplified signal;
e) a first phase-sensitive demodulator which demodulates the amplified signal with respect to the first reference waveform, producing a first demodulated signal;
f) a second phase-sensitive demodulator which demodulates the amplified signal with respect to the second reference waveform, producing a second demodulated signal;
g) filtering means for filtering the portion of the electrical signal created by electromagnetic radiation having the first wavelength and the portion of the electrical signal created by electromagnetic radiation having the second wavelength, said filtering means generating a first filtered signal which indicates the unadjusted amplitude measurement of the electromagnetic radiation having the first wavelength and a second filtered signal which indicates the unadjusted amplitude measurement of the electromagnetic radiation having the second wavelength;
h) processing means which receives and analyzes the first and second filtered signals for determining the oxygen saturation of the blood in said perfused tissue; and
i) error correction means for correcting for residual phase errors by:
1) briefly operating the oximeter allowing only those pulses of light corresponding to the first wavelength to be emitted;
2) during this time measuring the amplitudes of the first and second demodulated and filtered signals, and computing the fractional crosstalk of the first demodulated and filtered signal into the second; demodulated and filtered signal
3) briefly operating the oximeter allowing only those pulses of light corresponding to the second wavelength to be emitted;
4) during this time measuring the amplitudes of the first and second demodulated and filtered signals, and computing the fractional crosstalk of the second demodulated and filter signal into the first demodulated and filtered signal;
5) during normal operation, producing a corrected first signal by subtracting from the first demodulated and filtered signals a quantity equal to the second demodulated and filtered signal times the fractional crosstalk of the second demodulated and filtered signal into the first demodulated and filtered signal; and
6) during normal operation, producing a second corrected signal by subtracting from the second demodulated and filtered signal a quantity equal to the first demodulated and filtered signal times the fractional crosstalk of the first demodulated and filtered signal into the second demodulated and filtered signal.

3. A pulse oximeter comprising:
1) a waveform generator producing a first drive waveform, a first reference waveform having the same frequency and initially the same phase as the first drive waveform, a second drive waveform, and a second reference waveform having the same frequency and initially the same phase as the second drive waveform, the second waveforms being identical in frequency and waveshape to the first waveforms but differing in phase by 90 degrees;
2) first and second electro-optical emitters respectively energized by the first and second drive waveforms, said first and second electro-optical emitters producing electromagnetic radiation having first and second wavelengths, respectively;
3) a photodetector responsive to radiation of said first and second wavelengths and arranged to receive radiation from said first and second emitters after said radiation has interacted with body tissue;
4) an amplifier for receiving a signal generated by said photodetector and for producing an amplified signal;
5) a first phase-sensitive demodulator which demodulates the amplified signal with respect to the first reference waveform, producing a first demodulated signal;
6) a second phase-sensitive demodulator which demodulates the amplified signal with respect to the second reference waveform, producing a second demodulated signal;
g) filtering means for filtering the portion of an electrical signal created by electromagnetic radiation having the first wavelength and the portion of the electrical signal created by electromagnetic radiation having the second wavelength, said filtering means generating a first filtered signal which indicates the unadjusted amplitude measurement of the electromagnetic radiation having the first wavelength and a second filtered signal which indicates the unadjusted amplitude measurement of the electromagnetic radiation having the second wavelength;
i) processing means which receives and analyzes the first and second filtered signals for determining the oxygen saturation of the blood in said perfused tissue; and
j) error correction means for correcting for residual phase errors by:
a) briefly operating the oximeter allowing only those pulses of light corresponding to the first wavelength to be emitted;
b) during this time iteratively adjusting the phase of the second reference signal to produce a null on the output of the second demodulator;
c) briefly operating the oximeter allowing only those pulses of light corresponding to the second wavelength to be emitted;
d) during this time iteratively adjusting the phase of the first reference signal to produce a null on the output of the first demodulator;

e) during normal operation, producing a corrected first signal by operating the first demodulator with the adjusted phase of the first reference signal; and f) during normal operation, producing a second corrected signal by operating the second demodulator with the adjusted phase of the second reference signal.

4. Apparatus for use in a pulse oximeter for generating and detecting two wavelengths of electromagnetic radiation comprising:

(a) means for generating pulses of electromagnetic radiation having a first wavelength and for generating pulses of electromagnetic radiation of a second wavelength that have the same frequency as the pulses having the first wavelength and are in quadrature with the pulses having the first wavelength;

(b) means for simultaneously exposing a selected portion of a human being or animal to the first and second pulses;

(c) detector means for producing an electrical signal which is representative of the electromagnetic radiation intensity at a selected location in the vicinity of the selected portion of the human being or animal, said detector means being responsive to electromagnetic radiation including the first and second wavelengths;

(d) amplifying means for amplifying the electrical signal;

(e) demodulating means for extracting the portion of the electrical signal created by electromagnetic radiation having the first wavelength and for extracting the portion of the electrical signal created by electromagnetic radiation having the second wavelength;

(f) filtering means for filtering the portion of the electrical signal created by electromagnetic radiation having the first wavelength and the portion of the electrical signal created by electromagnetic radiation having the second wavelength, said filtering means generating a first filtered signal which indicates the unadjusted amplitude measurement of the electromagnetic radiation having the first wavelength and a second filtered signal which indicates the unadjusted amplitude measurement of the electromagnetic radiation having the second wavelength; and (g) error compensation means which corrects residual phase errors by:

1) briefly operating the oximeter allowing only those pulses of light corresponding to the first wavelength to be emitted;

2) during this time adjusting the phase of the second reference signal to produce a null on the output of the demodulating means 3) briefly operating the oximeter allowing only those pulses of light corresponding to the second wavelength to be emitted;

4) during this time adjusting the phase of the first reference signal to produce a null on the output of the demodulating means;

5) during normal operation, producing a corrected first signal by operating the demodulating means with the adjusted phase of the first reference signal; and 6) during normal operation, producing a second corrected signal by operating the demodulating means with the adjusted phase of the second reference signal.

5. The pulse oximeter as claimed in claim 4, wherein the filtering means comprises a bandpass filter and wherein the error compensation means corrects residual phase errors through adjustment of the bandpass filter.

6. A method for performing pulse oximetry wherein a selected portion of a human being or an animal is exposed to electromagnetic radiation of two different wavelengths, wherein the improvement comprises:

a) generating a first pseudorandom pulse sequence of electromagnetic radiation at a first wavelength and a second pseudorandom pulse sequence at a second wavelength, wherein said first pseudorandom pulse sequence and said second pseudorandom pulse sequence are orthogonal;

b) simultaneously exposing the selected portion of the human being or animal to the first and second pseudorandom radiation pulse sequences;

c) producing an electrical signal corresponding to the electromagnetic radiation intensity in a band of wavelengths including said first and second wavelengths, wherein said electrical signal is received at a selected location in the vicinity of the selected portion; and d) demodulating the electrical signal by means of a first demodulator producing a first wavelength signal and a second demodulator producing a second wavelength signal, wherein the first demodulator demodulates using a first reference signal, the second demodulator demodulates using a second reference signal, said first reference signal corresponds to the first pseudorandom sequence and said second reference signal corresponds to the second pseudorandom sequence.

\* \* \* \* \*